US009263500B2

(12) United States Patent
Humbert et al.

(10) Patent No.: US 9,263,500 B2
(45) Date of Patent: Feb. 16, 2016

(54) INTEGRATED CIRCUIT COMPRISING A GAS SENSOR

(71) Applicant: ams International AG, Rapperswil-Jona (CH)

(72) Inventors: Aurelie Humbert, Brussels (BE); Roel Daamen, Herkenbosch (NL); Viet Hoang Nguyen, Lueven (BE)

(73) Assignee: ams International AG, Rapperswil-Jona (CH)

( * ) Notice: Subject to any disclaimer, the term of this patent is extended or adjusted under 35 U.S.C. 154(b) by 0 days.

(21) Appl. No.: 13/852,978

(22) Filed: Mar. 28, 2013

(65) Prior Publication Data

US 2013/0256825 A1    Oct. 3, 2013

(30) Foreign Application Priority Data

Mar. 30, 2012 (EP) ................................. 12162383

(51) Int. Cl.
| | |
|---|---|
| *G01N 9/00* | (2006.01) |
| *H01L 27/16* | (2006.01) |
| *G01N 27/18* | (2006.01) |
| *H01L 37/00* | (2006.01) |
| *G01N 33/00* | (2006.01) |

(52) U.S. Cl.
CPC ................. *H01L 27/16* (2013.01); *G01N 27/18* (2013.01); *H01L 37/00* (2013.01); *G01N 33/004* (2013.01)

(58) Field of Classification Search
CPC ............ G01N 27/128; G01N 33/1826; G01N 27/121; G01N 27/125; G01N 33/18; H01L 2924/1461; H01L 2224/73265; H01L 2224/92247
USPC ................ 257/414, 750, 758, 760; 73/31.06; 438/622
See application file for complete search history.

(56) References Cited

U.S. PATENT DOCUMENTS

| | | | |
|---|---|---|---|
| 8,648,395 B2 | 2/2014 | Cummins | |
| 2005/0218465 A1 | 10/2005 | Cummins | |
| 2006/0154401 A1* | 7/2006 | Gardner et al. | 438/53 |
| 2006/0185980 A1* | 8/2006 | Fukuda | 204/431 |
| 2008/0303532 A1 | 12/2008 | Nakakubo | |
| 2009/0050493 A1 | 2/2009 | Saji et al. | |
| 2011/0226041 A1* | 9/2011 | Cummins | 73/25.01 |

(Continued)

FOREIGN PATENT DOCUMENTS

| | | |
|---|---|---|
| CN | 101368921 A | 2/2009 |
| CN | 101416049 A | 4/2009 |

(Continued)

OTHER PUBLICATIONS

Yu, Tak For; "Gas Flow in Microchannels with Cavities—A Thesis"; 74 pages (Aug. 2003).

(Continued)

*Primary Examiner* — Armando Rodriguez
*Assistant Examiner* — Mohammed R Alam
(74) *Attorney, Agent, or Firm* — McDermott Will & Emery LLP

(57) ABSTRACT

An integrated circuit and a method of making the same. The integrated circuit includes a semiconductor substrate having a major surface. The integrated circuit also includes a thermal conductivity based gas sensor having an electrically resistive sensor element located on the major surface for exposure to a gas to be sensed. The integrated circuit further includes a barrier located on the major surface for inhibiting a flow of the gas across the sensor element.

8 Claims, 5 Drawing Sheets

(56) References Cited

U.S. PATENT DOCUMENTS

| | | | |
|---|---|---|---|
| 2011/0230068 A1* | 9/2011 | Pahl | ............................... 439/65 |
| 2012/0176223 A1 | 7/2012 | Ito | |

FOREIGN PATENT DOCUMENTS

| | | | |
|---|---|---|---|
| EP | 0 076 935 A2 | | 4/1983 |
| EP | 2554980 A1 | | 2/2013 |
| EP | 2554981 A1 | | 2/2013 |
| EP | 2559996 A1 | | 2/2013 |
| EP | 2 645 091 A1 | | 10/2013 |
| JP | H0196549 A | | 4/1989 |
| JP | H05223770 A | | 8/1993 |
| JP | 8 005597 A | | 1/1996 |
| JP | 08005597 | * | 1/1996 |
| JP | H085597 A | | 1/1996 |
| JP | 8 110317 A | | 4/1996 |
| JP | H08159836 A | | 6/1996 |
| JP | 2007-535662 A | | 12/2007 |
| JP | 2008304237 A | | 12/2008 |
| JP | 2009-099760 A | | 5/2009 |
| JP | 2010533840 A | | 10/2010 |
| WO | 00/45163 A2 | | 8/2000 |
| WO | 2005/095936 A | | 10/2005 |
| WO | 2011037234 A1 | | 3/2011 |

OTHER PUBLICATIONS

Microsens SA; "Microsens Thermal Conductivity Sensor—MTCS-2202, Natural Gas (Methane) Sensor)"; 4 pages. (2007).

e2v Technologies; "Pellistor Application Note 5 Thermal Conductivity Sensors"; A1A-Pellistor_AN5 Issue 1; 2 pages (Mar. 2007).

Hach; "Process Analysis Thermal Conductivity Sensor Orbisphere 31XX"; Product Information; 2 pages (Dec. 2009).

Memscyclopedia.org; "SU-8: Thick Photo-Resist for MEMS"; retrieved from the internet Jan. 28, 2012 http://memscyclopedia.org/su8.html.

Kaanta, B. C., et al; "Effect of Forced Convection on Thermal Distribution in Micro Thermal Conductivity Detectors; Effect of Forced Convection on a Thermal Distribution in Micro TCDs"; J. Micromechanics & Microengineering, Int. of Physics Publishing, Bristol, GB, vol. 21, No. 4; pages (Mar. 10, 2011).

Sun, Jianhai et al.; "Design, Modeling, Microfabrication and Characterization of Novel Micro Thermal Conductivity Detector"; Sensors and Actuators B: Chemical: Intl. J. Devoted to Research and Develp. of Physical and Chemical Transducters, Elsevier S.A. Switzerland; vol. 160, No. 1; pp. 936-941 (Sep. 3, 2011).

Nemoto Sensor Engineering Co., LTD; "NAP-21"; retrieved from the Internet Jan. 31, 2013 http://www.nemoto.co.jp/en/products/sensor/residential/NAP-21A.html; 2 pages (Nov. 2012).

Extended European Search Report for application No. 12162383.9 (Jul. 10, 2012).

Office action from counterpart application CN 201310098655.2 (Feb. 2, 2015).

Briand, D. et al., "Autonomous Sensors on Flexible Foils Powered by RFID and Energy Scavenging for Environmental and Goods Monitoring" Proceedings of Power MEMS2008+ micro EMS 2008, Sendai, Japan, Nov. 9-12, 008 pp. 173-176, XP055214453.

* cited by examiner

INTEGRATED CIRCUIT COMPRISING A GAS SENSOR

CROSS-REFERENCE TO RELATED APPLICATIONS

This application claims the priority under 35 U.S.C. §119 of European patent application no. 12162383.9, filed on Mar. 30, 2012, the contents of which are incorporated by reference herein.

BACKGROUND OF THE INVENTION

This invention relates to an integrated circuit. In particular, this invention relates to an integrated including a gas sensor. The invention further relates to a method of making such an integrated circuit.

Nowadays, integrated circuits may comprise a plethora of different sensors, such as gas sensors, relative humidity (RH) sensors, specific analyte detection sensors, and so on.

Gas sensors are used in a number of different applications to sense the composition and/or concentration of various gases. One example application is in the field of supply chain monitoring, in which the levels of $CO_2$ present in the air surrounding consumables such as food or beverages is monitored to determine suitability for consumption. The monitoring may typically be carried out at various stages in the distribution chain. Other applications include air quality monitoring, use in heating, ventilation and air conditioning (HVAC) system in buildings or automobiles, or $CO_2$ monitoring in greenhouses.

It is particularly relevant to mass market applications such as RF tags for product monitoring that the gas sensor functionality can be added to the integrated circuit with limited additional cost, as there is a large price pressure on such integrated circuits; i.e. they have to be produced cheaply in order to be commercially attractive.

FIG. 1 illustrates an example of an integrated circuit including a gas sensor. The integrated circuit includes a substrate 2 into which may be incorporated a number of active components such as CMOS devices. As is well known in the field of integrated circuit manufacture, above the substrate there is be provided a metallization stack 4 incorporating a plurality of metallic layers separated by a plurality of insulating layers. The metal layers provide interconnections between the active components in the substrate 2, and typically comprise metals such as aluminium or copper.

In this example, the gas sensor is provided above the metallization stack 4. In particular, the gas sensor is located above a series of passivation layers 16A, 16B and 18, which are themselves conventionally located on top of the stack 4. In the present example, layers 16A and 16B comprise High Density Plasma (HDP) oxide, while the layer 18, which provides scratch protection, comprises a thick layer of $Si_3N_4$. As shown in FIG. 1, metal vias 8 pass through the passivation layers to connect electrodes 15 of the gas sensor to the metallization stack 4. This allows electrical connection to be made between the gas sensor and one or more of the active components in the substrate 2 via the metallization stack 4. The vias 8 and electrodes 15 may comprise the same material as the metal layers in the metallization stack 4, or can alternatively comprise a different material, such as Tungsten.

Also shown in FIG. 1 is a protection layer 14, comprising for example $Ta_2O_5$, which provides protection against corrosion of the electrodes 15.

Above the protection layer 14 there is provided a thick oxide layer 17. Through the oxide layer 17, protection layer 14, and the passivation layers 16A, 16B and 18, there is provided a trench 20 at the bottom of which is provided a bond pad 12 in an upper metallization layer of the metallization stack 4. The trench 20 thus enables electrical connections to be made to the integrated circuit through the various insulating upper layers.

The gas sensor itself comprises a sensor element 8, which is shown in cross section in FIG. 1. The sensor element 8 typically comprises a metallic material, for example Tungsten. In an alternative embodiment, the sensor element 8 may comprise a semiconducting material such as doped polysilicon. The sensor element 8 may be arranged in, for example, a meander pattern for increased surface area (resulting in greater sensitivity). As shown in FIG. 1, the ends of the meander pattern pass through the protection layer 14 to connect to the sensor electrodes 15. Also as shown in FIG. 1, the meander pattern itself is located substantially within a shallow trench formed in the oxide layer 17. The sensor element 8 is thus presented to the surrounding environment for direct access to a gas to be sensed.

Thus, FIG. 1 constitutes an example of a gas sensor provided in an integrated circuit above the passivation stack on a metallization stack which is itself provided above active components such as CMOS transistors in a semiconductor substrate 2.

The gas sensor is thermal conductivity based, and operates as follows. A current is passed through the sensor element 8, causing the sensor element 8 to heat up. The surrounding gas carries heat away from the sensor element 8. The amount of heat that is transferred, and the rate at which it is transferred, is dependent upon the composition of the gas. At thermal equilibrium, the resistivity of the sensor element 8 (which is dependent upon the temperature of the sensor element 8) is sensitive to the amount and rate of heat transfer. In turn therefore, the resistivity of the sensor element 8 is dependent upon the composition of the surrounding gas. In this way, by making resistivity measurements of the sensor element 8, the composition of the surrounding gas can be determined.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided an integrated circuit. The integrated circuit includes a semiconductor substrate having a major surface. The integrated circuit also includes a thermal conductivity based gas sensor having an electrically resistive sensor element located on the major surface for exposure to a gas to be sensed. The integrated circuit further includes a barrier located on the major surface for inhibiting a flow of the gas across the sensor element.

According to another aspect of the invention, there is provided a method of making an integrated circuit. The method includes providing a semiconductor substrate having a major surface. The method also includes forming a thermal conductivity based gas sensor having an electrically resistive sensor element located on the major surface for exposure to a gas to be sensed. The method further includes forming a barrier on the major surface for inhibiting a flow of the gas across the sensor element.

The provision of a barrier for inhibiting a flow of the gas across the sensor element mitigates against the effects of cooling and relative humidity as described in further detail below. This allows a more accurate and reliable measurements of gas concentration/composition to be made.

In one embodiment, the sensor element is located in a trench in a metallization stack on the major surface. This allows the sensor element conveniently to be formed from one or more metal and or via layer features in the metallization stack. The trench itself forms the barrier to gas flow across the sensor element.

In one example, the sensor element is formed in a lower level of the metallization stack. By providing the sensor element in a lower level of the stack the sensor element can be distanced appropriately from a flow of gas across the top of the trench. In some examples, a heater element for heating the gas to be sensed, can be is located in the trench along with the sensor element.

In one embodiment, the integrated circuit can include a patterned layer located on the major surface of the substrate. The patterned layer can form at least part of the barrier. For example, the patterned layer can be located on the metallization stack, and the trench and the patterned layer can together form the barrier. Alternatively, in embodiments where the sensor element is not provided in a trench in a metallization stack, the patterned layer alone can provide the barrier. The patterned layer can comprise a photoresist material such as SU-8. This allows the shape (e.g. height and depth) and position of the barrier to be defined using well establish photolithography techniques.

A depth of the cavity formed by the patterned layer can be at least 10 µm. A cavity formed by the patterned layer can have an aspect ratio depth:width, where width is about equal to 1 µm and where depth (d) is in the range of about 30 µm to about 15 µm (e.g., 30 µm≤d≤15 µm).

According to a further aspect of the invention, there can be provided a Radio Frequency Identification (RFID) Tag including an integrated circuit of the kind described above.

According to another aspect of the invention, there can be provided a mobile communications device including an integrated circuit of the kind described above.

According to a further aspect of the invention, there can be provided a heating, ventilation and air conditioning (HVAC) system including one or more integrated circuits of the kind described above.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

In accordance with embodiments of this invention, it has been realised that gas flow across a sensor element in a gas sensor of the kind described above in relation to FIG. 1 can produce erroneous readings as regards the composition of the gas itself. In particular, it has been found that movement of the gas across the sensor element can lead to cooling of the sensor element at a greater rate than is typical when the gas surrounding the sensor element 8 is static. This increased cooling results from the fact that the flow of gas is able to carry heat away from the sensor element both by normal thermal conduction and also by the motion of the gas itself. Measurements illustrating this principle are shown in FIG. 2.

Figure 2:
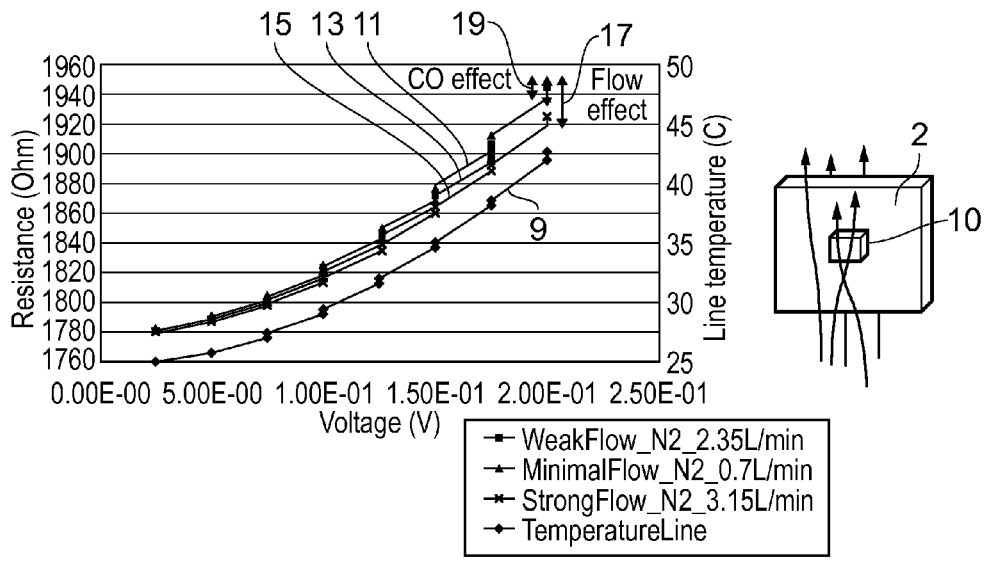
FIG. 2 illustrates the effect of a cooling flow of gas across a sensor of the kind shown in FIG. 1.

On the right hand side of FIG. 2 there is shown a schematic of a gas sensor 10 provided on a major surface of a substrate 2 of an integrated circuit. The arrows schematically indicate a of gas flow across the gas sensor 10.

Figure 1:
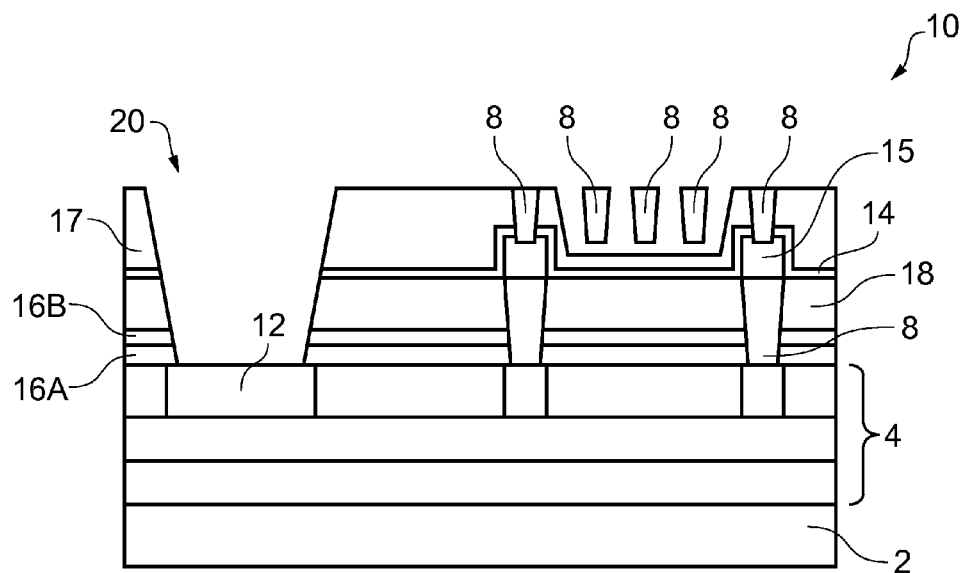
FIG. 1 shows an integrated gas sensor including a gas sensor.

The graph in FIG. 2 illustrates the resistance of a sensor element of the kind illustrated in FIG. 1 as a function of voltage across the sensor element, for 3 separate rates of gas flow across the sensor element. In particular, in the graph in FIG. 2, plot line 11 illustrates the resistance of the sensor element as a function voltage for a weak flow of gas across (0.7 liters/minute) the sensor element, while the plot line 13 (1.35 liters/minute) and plot line 15 (3.15 liters/minute) respectively illustrate the same plot for progressively stronger flows of gas. Plot line 9 indicates the correspondence between the resistance and wire temperature for the particular structure (material and design) of sensor element illustrated in FIG. 1.

Comparing particularly plot lines 11 and 15 (corresponding to the weakest and strongest flows measured), it is clear from FIG. 2 that for a stronger flow of gas, the resistance of the sensor element decreases for a given voltage across the sensor element. This decrease in resistance is caused by the increased cooling power of the gas as the strength of the flow across the sensor element increases. Because of this effect, it has been realised by the inventors that measurements of resistance across the sensor elements become degenerate in the sense that a given value of resistance can result from a combination of the composition of the gas with the rate of flow of the gas across the sensor.

In FIG. 2, multiple measurements of resistance were made at each voltage and at each flow rate, for different concentrations of $CO_2$ present in the surrounding gas. This allowed the magnitude of differences in resistance originating from gas composition to be compared with the effects of gas flow. The differences in resistance caused by different flow rates (indicated in FIG. 2 by the arrow labelled 17) were found to be somewhat larger than those caused by a change in the composition of the gas (indicated in FIG. 2 by the arrow labelled 19). This presents a significant problem when attempting to determine the composition of the gas, since it is difficult to factor out the effect of the gas flow, and in fact the effects of flow rate can substantially mask changes in gas composition.

Another effect that has been noted by the inventors is that the level of humidity in the gas surrounding the sensor element can also distort resistance measurements. This is illustrated in FIG. 3.

Figure 3:
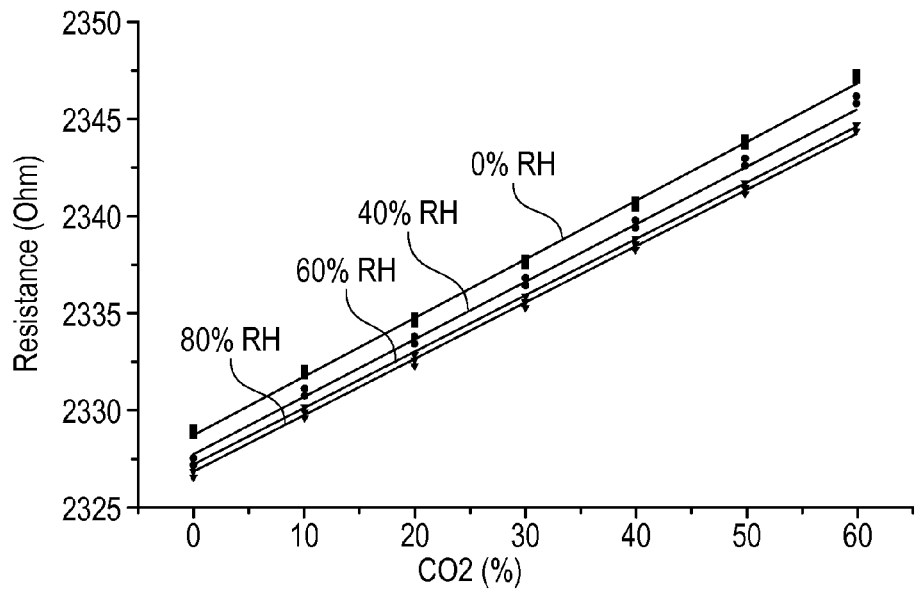
FIG. 3 illustrates the effect of changing relative humidity on a gas sensor of the kind shown in FIG. 1.

In FIG. 3, along the x axis is plotted gas concentration. In the present case the gas is $CO_2$. For a given relative humidity (RH) of the gas, the resistance of the sensor element indicates a corresponding $CO_2$ concentration. The four different plots in FIG. 3 illustrate that the functional relationship between the $CO_2$ concentration and the resistance of the sensor element shifts according to the relative humidity of the gas. Thus, at a relative humidity level of 0%, a given level of resistance in the sensor element tends to indicate a lower concentration of $CO_2$ than for, for example, a relative humidity of 40%, 60% or 80%.

In common with the problem described above relating to gas flow, the inventors have realised that the relative humidity of the gas causes the measurements of resistance in a sensor element of a thermal conductivity based gas sensor to become degenerate, since the resistance of the element depends both upon the concentration of the gas and the relative humidity of the gas. As with gas flow, it is difficult to factor out the effect of relative humidity, unless separate provision is made for determining the relative humidity in the gas itself.

In accordance with an embodiment of this invention, there is provided an integrated circuit including a thermal conductivity based gas sensor having an electrically resistive sensor element located on a major surface of a semiconductor substrate. To mitigate the above described effects of gas flow and/or relative humidity, the integrated circuit also includes a barrier, which is located on the major surface of the substrate. The barrier acts to inhibit the flow of gas across the sensor element.

Figure 4:
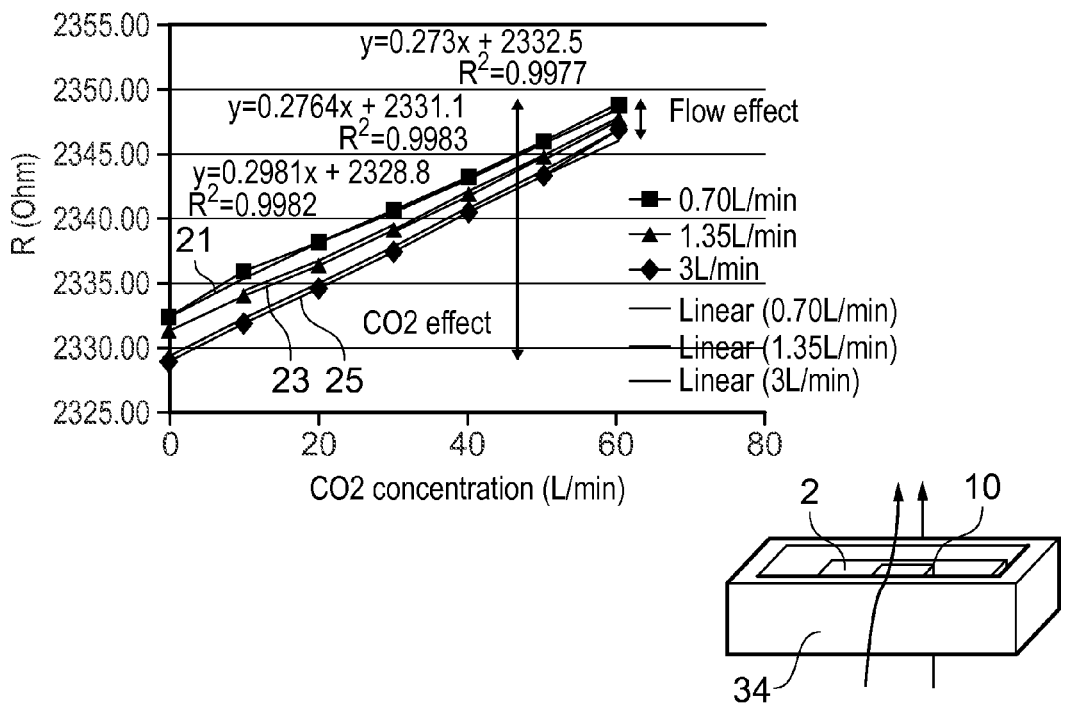
FIG. 4 illustrates the principal of providing a barrier gas flow across a gas sensor.

In FIG. 4, it is demonstrated that by providing barrier against a flow of gas across a sensor element, the differences in resistance caused by gas flow can be made substantially smaller than the differences in resistance caused by changes in gas composition/concentration.

To the right of FIG. 4 is shown a schematic example of a gas sensor 10 provided on a substrate 2. Again, gas flow is schematically indicated by the series of arrows. In this example, the gas flow itself is inhibited by a barrier 34.

In the graph on the left hand side of FIG. 4, $CO_2$ concentration is shown as a function of the resistance of the sensor element. Again, three separate plots are provided: plot line 21 illustrates a relatively low flow rate (0.7 liters/minute), while plot line 23 (1.35 liters/minute) and plot line 25 (3 liters/minute) illustrate successively higher flow rates.

Although in FIG. 2 the apparent $CO_2$ concentration is still affected by gas flow rate across the sensor element (demonstrated by the different positions of the three different plots), it is noted that the effect of gas flow in cooling the sensor element is substantially smaller than the effect shown in FIG. 2. In fact, these measurements illustrate that by using a barrier, the effect of gas flow across a sensor element can be made relatively small compared to the effect of changes in gas concentration whereby the degeneracy of resistance measurements in the sensor element noted above is substantially mitigated.

In addition to mitigating the cooling effects of gas flow, it is also anticipated that the provision of a barrier can mitigate the effects of relative humidity. Due to the presence of the barrier, the gas surrounding the sensor element relatively static. When the sensor element is heated, humidity in the gas dissipates and, since the gas is static, is not replaced by humidity in a new volume of gas arriving at the sensor. Therefore, heating of the sensor element itself reduces the effect of humidity on the thermal conductivity of the gas to be sensed.

Figure 5:
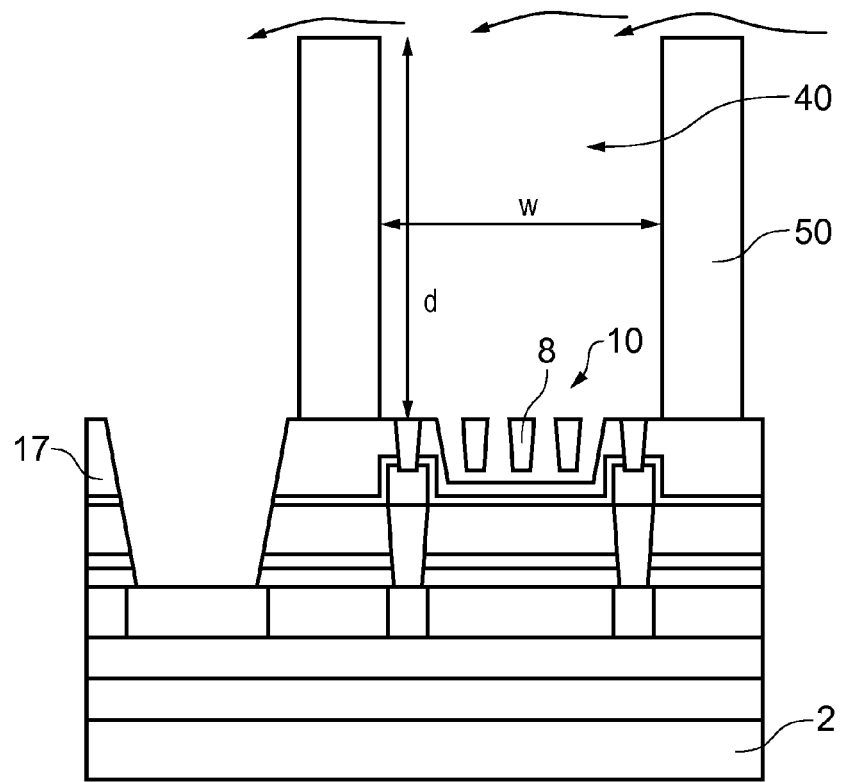
FIG. 5 shows an example of an integrated circuit according to an embodiment of the invention.

FIG. 5 illustrates a first example of an integrated circuit according to an embodiment of the invention. It will be appreciated that the example in FIG. 5 is similar to the device described above in relation to FIG. 1.

In addition to the various metallization, passivation and other features described in FIG. 1, the integrated circuit in this example is provided with a barrier 50. The barrier has a height d and width w. The barrier acts to inhibit gas flow across the sensor element 8. Instead, the flow of gas illustrated by the arrows at the top of FIG. 5 passes over the top of the barrier. In contrast, in the example of FIG. 1, gas is able to flow directly across the top of the sensor element 8, leading to the cooling and humidity effects noted above.

Although the barrier 50 prevents direct gas flow across the sensor element 8, the sensor element 8 still has direct access to the surrounding environment for sensing of the relevant gas. Thus the barrier does not completely enclose the sensor element. As described above, the barrier prevents cooling of the sensor element and/or the effects of relative humidity due to gas flow, thereby improving the reliability and accuracy of measurements of resistivity in the sensor element 8.

In the example of FIG. 5, the barrier 50 is formed using a patterned layer formed above the oxide layer 17. The patterned layer can be provided using standard lithography techniques, following the formation of the metallization stack and various passivation layers and the sensor itself. Any suitable configuration for the barrier 50 can be provided. For example, it would be possible to provide a barrier patterned such that it can provide protection against gas flow for one or even a plurality of separate sensors in an integrated circuit. In one example, the patterned layer forming the barrier 50 can comprise a polymer such as a photo-sensitive polymer. An example of such a material is SU-8. Such a layer can be patterned using standard photolithography techniques.

In accordance with an embodiment of the invention, the depth of the cavity formed by a patterned layer of the kind described above, is at least 10 microns. It is anticipated that this depth is sufficient to distance the sensor element far enough away from the gas flow to mitigate much of the effects of cooling and/or relative humidity.

The cavity can also be formed having an aspect ratio depth:width that is sufficiently deep to again ensure that the flow of gas is kept separate from the sensor element 8. In particular, where the width of the cavity=1, a suitable depth is in the range $30 \leq d \leq 15$.

Figure 6:
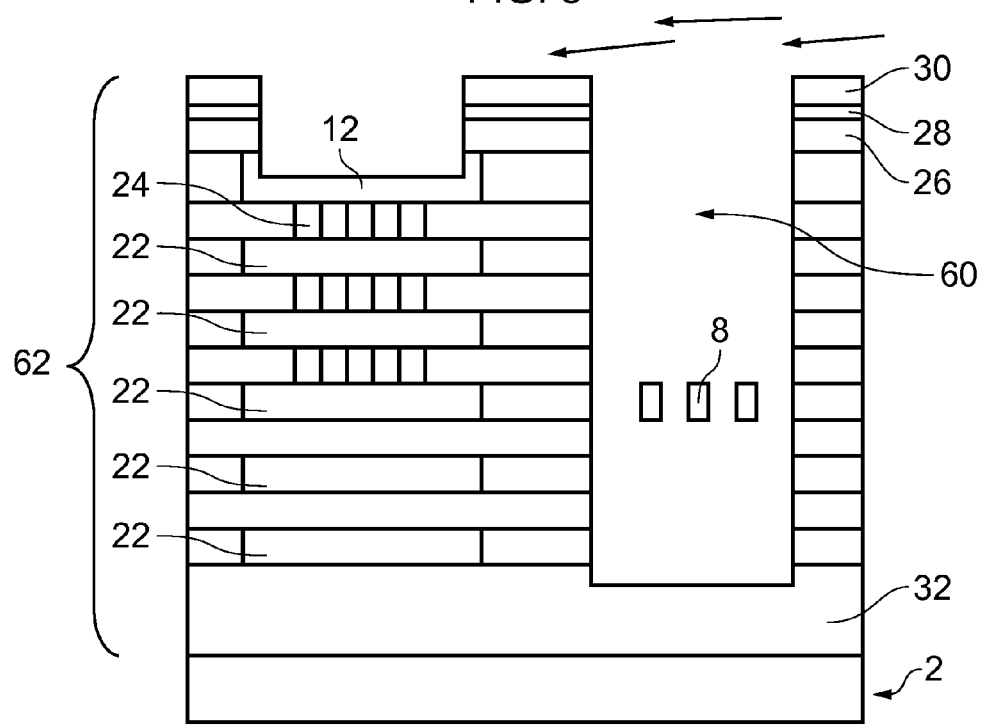
FIG. 6 shows another example of an integrated circuit according to an embodiment of the invention.

FIG. 6 illustrates a second example of an integrated circuit incorporating a gas sensor in accordance with an embodiment of the invention. In this example, the sensor element 8 comprises metal features formed in a metal layer of a metallization stack 62 provided on a semiconductor substrate 2. As shown in FIG. 6, the metallization stack 62 can comprise a number of separate layers 22 separated by layers of insulating material. The metal layers 22 can be interconnected by metal vias 24 which pass through the insulating layers. Above the stack 62 can be provided one or more passivation or other layers 26, 28, 30.

To the left of the metallization stack 62 shown in FIG. 6, it is illustrated that an opening can be made through the one or more passivation or other layers 26, 28, 30 to provide access to a bond pad 12. The bond pad 12 in this example is formed from one of the metal layers in the metallization stack 62 and can be interconnected to other metal layers in the stack using vias 24 as described above. To the right of the example shown in FIG. 6, it is shown that a trench 60 can be formed through the various layers in the metallization stack. This trench can be formed using, for example, standard etching techniques during formation of the metallization stack 62.

In the present example, the trench 60 forms the barrier of the integrated circuit that inhibits gas flow across the sensor element 8. The flow of gas across the top of the integrated circuit is shown by the arrows at the top of the trench in FIG.

6. Note that in contrast to the example of FIG. 1, in which gas is able to flow directly across the top of a sensor element which is located at the top of a shallow trench, in the embodiment of FIG. 6, the flow of gas cannot directly reach the sensor element 8.

In the present example, the sensor element 8 itself is formed from a metallic material in one of the metal levels of the metallization stack 62. Accordingly, the sensor element 8 can conveniently be laid down as part of the metallization stack during metal processing of the integrated circuit in accordance with normal back end of line (BEOL) processes. This makes for convenient and cost effective formation of the gas sensor on top of a semiconductor integrated circuit comprising a substrate incorporating, for example CMOS devices.

As described in more detail below, in an alternative example, the sensor element 8 may be provided in one of the via levels of the device instead of one of the metal levels. Typically, the metal features in the via levels may comprise a different metal to that which is used in the metal levels. By way of example, where the metal levels may comprise Aluminium, the via levels may comprise Tungsten. The material used to form the sensitive element 8 may thus differ, according to the level in which it is provided.

Figure 7:
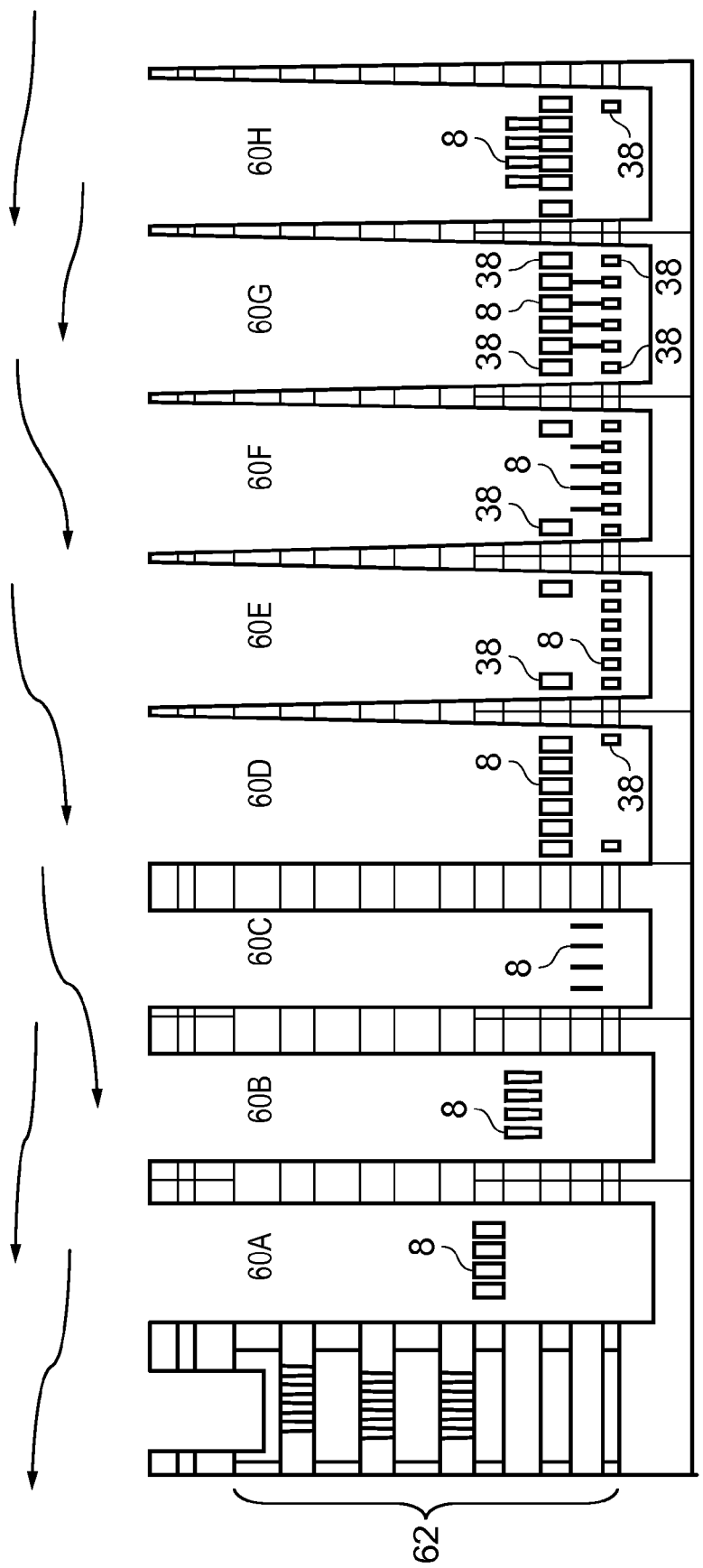
FIG. 7 schematically illustrates a number of different trench configurations that may be implemented in an integrated circuit of the kind shown in the embodiment of FIG. 6.

FIG. 7 illustrates a number of different configurations for a gas sensor comprising a sensor element 8 located in a trench in accordance with the example described above in relation to FIG. 6. In FIG. 7, it is not envisaged that all of the separate example trench configurations would be provided in a single device. Indeed, a typical embodiment may only include a single trench. Instead, the various trench configurations are shown here side by side for the purpose of illustrating that a large number of different configurations are possible.

Thus, in the trench 60a shown in FIG. 7, the sensor element 8 is provided in one of the metal levels of the metallization stack 62 in much the same way as shown in FIG. 6. In trench 60b in FIG. 7, the sensor element 8 is provided instead in a via level located between two different metal levels also as described above in relation to FIG. 6.

In trench 60c, the sensor element is again shown to be provided in a via level, however in this example the sensor element 8 is thinner than the sensor element 8 shown in the via level of trench 60b. The surface area to volume ratio of the sensor element 8 in the trench 60c is thereby increased, increasing sensitivity. Design rules typically differ between the different levels in a metallization stack. The level in which the sensor element is located may therefore be chosen according to the minimum line dimensions allowed.

In one or more embodiments of the invention, in addition to providing a sensor element 8 in the trench, it is also possible to provide a separate heater element 38. As is known in the art, in certain thermal conductivity based gas sensors, it is possible to heat the gas to be sensed using not the sensor element itself but instead with a separate heater element. This aside, the functioning of the centre is substantially similar to that described above, at least insofar as resistance measurements on the sensor element are sensitive to the thermal conductivity of the surrounding gas and the rate at which heat can be carried away from the sensor element 8.

Thus, in trench 60d shown in FIG. 7, the sensor element 8 is provided in a metal level of the metallization stack 62, while a separate heater 38 is provided in a different metal level. In the trench 60e in FIG. 7, the locations of the sensor element 8 and the heater element 38 are switched, such that the sensor element 8 is located below the heater element 38.

In the example trench 60f in FIG. 7, the configuration is similar to that shown in trench 60e, but it is illustrated that the sensor element can be formed not just in a single metal or via layer, but can comprise features from neighbouring metal or via layers. Thus, the sensor element 8 in trench 60f comprises portions made from a metal layer in addition to portions from a neighbouring via layer located directly above the metal layer.

In the example of FIG. 60g, again the sensor element 8 comprises features from more than one layer in the metallization stack. In particular the sensor element 8 comprises portions from two neighbouring metal layers of the stack 62 in addition to portions from an intervening via layer which electrically connects the portions from the neighbouring metal layers. Also illustrated in trench 60g is a heater 38. In this example, the heater 38 is not provided in a separate metal or via layer, but is instead incorporated into the same layer or layers as the one or more layers in which the sensor element 8 is provided.

Trench 60h is another example in which the heater 38 is provided in a separate level to that in which the sensor element is provided. Again, the sensor element 8 includes portions from adjacent levels.

Accordingly, it is clear from FIG. 7 that a wide variety of different configurations is possible. The high degree of freedom in designing these different configurations is provided at least in part by the provision of the gas sensor and/or heater element in a metallization stack, whereby well known and easily controllable metallization techniques can be employed when manufacturing the sensor.

Figure 8:
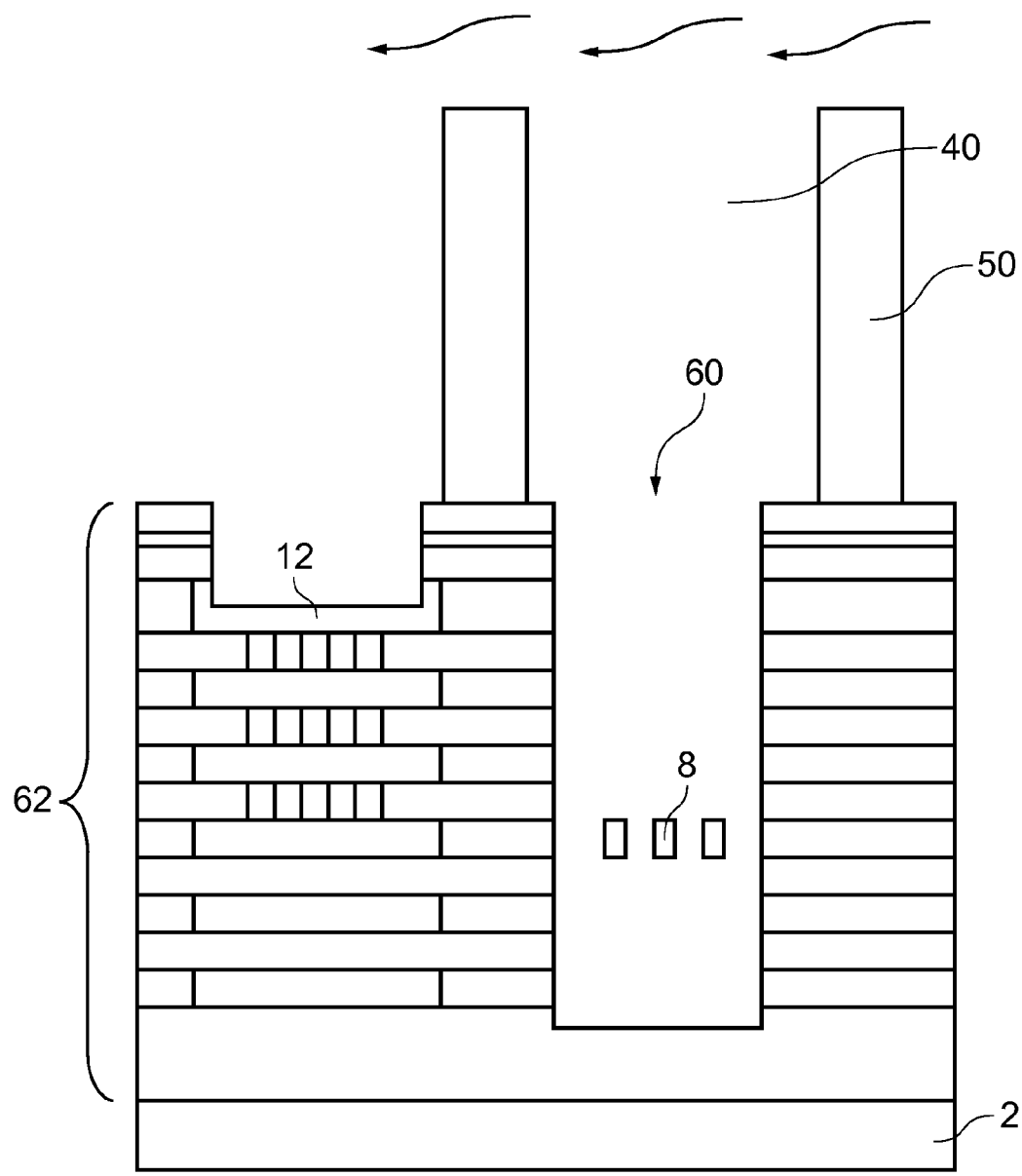
FIG. 8 shows a further example of an integrated circuit according to an embodiment of the invention.

A further embodiment of the invention is illustrated in FIG. 8. The embodiment in FIG. 8 is similar to the embodiment in FIG. 6. Thus, as shown in FIG. 8, the sensor element 8 is provided in a trench 60 in a metallization stack 62. The configuration of the sensor and/or heater element in the trench 60 can follow any of the examples described above in relation to FIG. 7.

The embodiment in FIG. 8 differs from the embodiment described above in relation to FIG. 6 insofar as in addition to providing the sensor element and/or heater element in a trench 60 in a metallization stack 62, a patterned layer can be provide above one or more passivation layers on the metallization stack 62. The patterned layer forms a further barrier 50. In this way, the patterned layer cooperates with the trench 60 to provide an enhanced barrier. Since the gas flow illustrated in FIG. 8 by the arrows at the top of the patterned layer is further removed from the sensor element than it would be in the absence of the patterned layer, the sensitivity of the sensor element 8 to gas flow and relative humidity is further reduced. The patterned layer can be formed in much the same way as the patterned layer described above in relation to FIG. 5.

Typical materials for the sensor elements described herein include metallic materials such as Al and W. Alternative materials also include Cu, Ti, TiN , Ta, TaN, Pt, or semiconductor materials such as polysilicon.

It will be appreciated that where the sensor element 8 is provided in a trench 60 in a metallization stack of the kind described above, it is possible that the position of the element 8 can be chosen to be near to the bottom of the trench, thereby distancing the element 8 from gas flow more so than it would be if the sensor were provided in a higher metallization layer in the stack. By providing the sensor element and/or heater element in a lower metal or via level of the metallization stack, the accuracy and sensitivity of the gas sensor can thereby be improved. Nevertheless, referring back to FIG. 8, the provision of a barrier 50 formed from a patterned layer located above a trench 60 in a metallization stack is advantageous in the sense that a barrier to gas flow can be formed even in the case where the sensor element is located in an upper metal or via layer of the trench 60.

Integrated circuits comprising gas sensors of the kind described herein can be manufactured using standard semiconductor processing techniques. For example, these techniques include the formation of metallization stacks using standard processes, and/or the provision of photo-resist materials above those metallization stacks using standard lithographic techniques.

Thus, a method of making an integrated circuit of the kind described herein can include providing a semiconductor substrate having a major surface and then forming a thermal conductivity based gas sensor having an electrically resistive sense element located on the major surface for exposure to a gas to be sensed. As noted above, the sensor element can in some examples be formed in a metallization stack, however this is not considered to be essential to the invention. The method of making an integrated circuit can further include forming a barrier on the major surface for inhibiting a flow, of the gas to be sensed, across the sense element. Also as noted above, the barrier can be formed by making a trench in a metallization stack and locating the sensor element within the trench. In an alternative example, the barrier can be formed using a patterned layer comprising, for example, photo-resist.

Applications of gas sensors according to the present invention include the provision in heating, ventilation and air conditioning (HVAC) systems. It is also envisaged that one or more gas sensors of the kind described herein can be incorporated into a radio-frequency identification (RFID) tag. Furthermore, an integrated circuit of the kind described herein can be incorporated into a mobile communications device.

Accordingly, there has been described an integrated circuit and a method of making the same. The integrated circuit includes a semiconductor substrate having a major surface. The integrated circuit also includes a thermal conductivity based gas sensor having an electrically resistive sensor element located on the major surface for exposure to a gas to be sensed. The integrated circuit further includes a barrier located on the major surface for inhibiting a flow of the gas across the sensor element.

Although particular embodiments of the invention have been described, it will be appreciated that many modifications/additions and/or substitutions may be made within the scope of the claimed invention.

The invention claimed is:

1. An integrated circuit comprising:
   a semiconductor substrate having a major surface;
   a metallization stack on the major surface;
   a trench in the metallization stack; and
   a thermal conductivity based gas sensor having an electrically resistive sensor element located in the trench for exposure to a gas to be sensed;
   wherein the trench forms a barrier located for inhibiting a flow of the gas across the sensor element;
   wherein the sensor element is formed in a metal level or via level of the metallization stack; and
   wherein the gas sensor further comprises a heater element, for heating the gas to be sensed, and wherein the heater element is located in the trench with the sensor element.

2. A Radio Frequency Identification (RFID) Tag comprising the integrated circuit of claim 1.

3. A mobile communications device comprising the integrated circuit of claim 1.

4. A heating, ventilation and air conditioning (HVAC) system comprising one or more integrated circuits according to claim 1.

5. An integrated circuit comprising:
   a semiconductor substrate having a major surface;
   a metallization stack on the major surface;
   a trench in the metallization stack; and
   a thermal conductivity based gas sensor having an electrically resistive sensor element located in the trench for exposure to a gas to be sensed;
   wherein the trench forms a barrier located for inhibiting a flow of the gas across the sensor element; and
   a patterned layer is located on the metallization stack, and wherein the trench and the patterned layer together form the barrier;
   wherein the sensor element is formed in a metal level or via level of the metallization stack; and
   wherein the gas sensor further comprises a heater element for heating the gas to be sensed, and wherein the heater element is located in the trench with the sensor element.

6. The integrated circuit of claim 5, wherein the patterned layer comprises a photoresist material.

7. The integrated circuit of claim 5, wherein the patterned layer forms a cavity having an aspect ratio depth:width, where width is about equal to 1 μm and where depth d is in the range of about 30 μm to about 15 μm.

8. The integrated circuit of claim 7, wherein the depth of the cavity formed by the patterned layer is at least 10 μm.

* * * * *